United States Patent

Rahtz et al.

[11] Patent Number: 4,564,610
[45] Date of Patent: Jan. 14, 1986

[54] SUBSTITUTED 5H-PYRIMIDO[5,4-B]INDOLES

[75] Inventors: Dieter Rahtz; Andreas Huth; Ralph Schmiechen; Dieter Seidelmann; Wolfgang Kehr; Herbert H. Schneider, all of Berlin, Fed. Rep. of Germany; Claus T. Braestrup, Roskilde, Denmark

[73] Assignee: Schering Aktiengesellschaft, Berlin and Bergkamen, Fed. Rep. of Germany

[21] Appl. No.: 562,248

[22] Filed: Dec. 16, 1983

[30] Foreign Application Priority Data

Dec. 16, 1982 [DE] Fed. Rep. of Germany ....... 3246932

[51] Int. Cl.$^4$ ................... A61K 31/505; C07D 487/04
[52] U.S. Cl. ...................... 514/80; 514/235; 514/237; 514/267; 544/115; 544/244; 544/250
[58] Field of Search ...................... 424/251, 200, 248.5; 544/250, 115, 244; 514/80, 267, 235, 237

[56] References Cited

U.S. PATENT DOCUMENTS 3,635,975  1/1972  Kim et al. ...................... 424/251 X

FOREIGN PATENT DOCUMENTS 0018857  11/1980  European Pat. Off. ............ 424/251
0005317  2/1971  Japan ........................... 544/250
0525677  12/1976  U.S.S.R. ........................ 544/250

OTHER PUBLICATIONS

Sundberg, et al., J. Org. Chem., vol. 38, No. 19, pp. 3324–3330 (1973).
Senda, et al., Chemical Abstracts, vol. 83, 9964p (1975).
Sedova, et al., Chemical Abstracts, vol. 91, 175296g (1979).
Velezheva, et al., Chemical Abstracts, vol. 93, 204,584y (1980).
Dubovenko, et al., Chemical Abstracts, vol. 94, 121446z (1981).
Suvorov, et al., Chemical Abstracts, vol. 96, 85492s (1982).
Unangst, Chemical Abstracts, vol. 99, 212484e (1983).

Primary Examiner—Donald G. Daus
Assistant Examiner—Diana G. Rivers
Attorney, Agent, or Firm—Millen & White

[57] ABSTRACT

Substituted 5H-pyrimido[5,4-b]indoles of Formula I

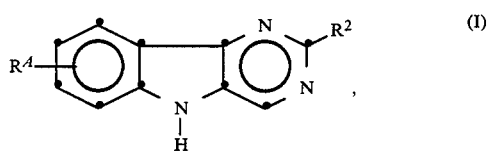

(I)

wherein
$R^2$ is halogen; the oxadiazolyl group

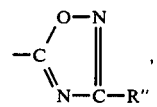

wherein
R" is lower alkyl with up to 3 carbon atoms; $C_{1-5}$-alkyl, cycloalkyl, aralkyl, or aryl; $OR^I$, $SO_nR^I$ with n being 0, 1, or 2, or

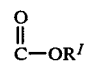

wherein $R^I$ is hydrogen, $C_{1-5}$-alkyl, cycloalkyl, aralkyl, or aryl;

wherein $R^{II}$ and $R^{III}$ are hydrogen, $C_{1-5}$-alkyl, $C_{3-5}$-alkenyl, cycloalkyl, aralkyl, aryl, or, with the connecting N-atom, a 5- or 6-membered heterocyclic ring; and
$R^4$ is hydrogen; the oxadiazolyl group

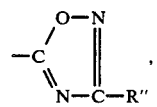

wherein R" is lower alkyl with up to 3 carbon atoms; halogen, nitro, $OR^I$, $SO_nR^I$ with n being 0, 1, or 2,

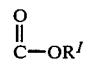

wherein $R^I$ is hydrogen, $C_{1-5}$-alkyl, cycloalkyl, aralkyl, or aryl;

wherein $R^{II}$ and $R^{III}$ are hydrogen, $C_{1-5}$-alkyl, cycloalkyl, $C_{3-5}$-alkenyl, aralkyl, aryl, or, with the connecting N-atom, a 5- or 6-membered heterocyclic ring; or

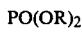

wherein R is $C_{1-5}$-alkyl, exhibit strong affinity for binding to benzodiazepine receptors.

The novel compounds are suitable for use in psychopharmaceutical preparations.

20 Claims, No Drawings

SUBSTITUTED 5H-PYRIMIDO[5,4-B]INDOLES

The present invention relates to novel substituted 5H-pyrimido[5,4-b]indoles, to pharmaceutical preparations containing them, and to processes for producing them.

SUMMARY OF THE INVENTION

It is an object of this invention to provide new valuable compounds having pharmacological activity.

Upon further study of the specification and appended claims, further objects and advantages of this invention will become apparent to those skilled in the art.

These objects have been achieved by this invention by providing substituted 5H-pyrimido[5,4-b]indoles of Formula I

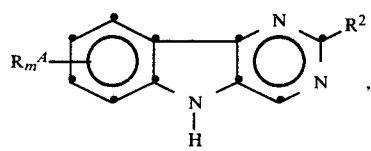

wherein
R$_2$ is the oxadiazolyl group

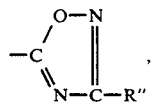

wherein
R" is lower alkyl with up to 3 carbon atoms; halogen, C$_{1-5}$-alkyl, cycloalkyl, aralkyl, aryl, OR$^I$, SO$_n$R$^I$

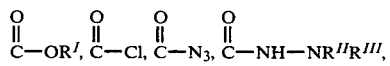

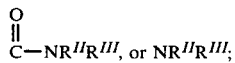

n is 0, 1, or 2;
m is 0, 1, 2, 3 or 4;
R$^I$ is hydrogen, C$_{1-5}$-alkyl, cycloalkyl, aralkyl, or aryl;
R$^{II}$ and R$^{III}$ each independently is hydrogen, C$_{1-5}$-alkyl, C$_{3-5}$-alkenyl, cycloalkyl, aralkyl, or aryl, or together with the connecting N-atom form a 5- or 6-membered heterocyclic ring;
R$^A$ is hydrogen, the oxadiazolyl group

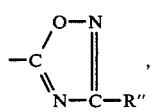

wherein R" is lower alkyl with up to 3 carbon atoms; halogen, nitro, OR$^I$, SO$_n$R$^I$,

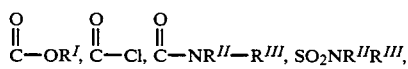

NR$^{II}$R$^{III}$, or PO(OR)$_2$,

R is C$_{1-5}$-alkyl, and
R$^I$, n, R$^{II}$ and R$^{III}$ are as defined above.

DETAILED DISCUSSION

The compounds of this invention possess valuable pharmacological properties. They especially affect the central nervous system and are suitable for use in psychopharmaceutical preparations.

The novel 5H-pyrimido[5,4-b]indoles of Formula I are substituted by R$^2$ in the 2-position and optionally by R$^A$ in the 6-, 7-, 8- and/or 9-position, R$^A$ preferably being in the 8- or 9-position or in the 8- and 9-positions when it is non-H.

Unless indicated otherwise, halogen within the scope of the present invention includes fluorine, chlorine, bromine, and iodine.

Alkyl includes straight chained and branched groups of up to 5 carbon atoms. Examples include methyl, ethyl, n-propyl, isopropyl, n-butyl, isobutyl, sec-butyl, t-butyl, n-pentyl, isopentyl, etc. Suitable alkenyl groups include those of 3–5 carbon atoms, especially allyl, and generally those based on the corresponding alkyl groups mentioned above.

Suitable cycloalkyl groups include those of 3–7 carbon atoms, for example cyclopentyl and cyclohexyl. Suitable aryl groups are of 5–10 carbon atoms, usually 6–10 and are generally hydrocarbons, for example phenyl, or 1- or 2-naphthyl. Suitable aralkyl groups are of 7–11 (or 7–10) carbon atoms, for example benzyl and styryl, e.g., wherein the aryl portion is as described above and the alkyl portion is as described above.

Suitable 5- or 6-membered heterocyclic rings NR$^{II}$R$^{III}$ include saturated and unsaturated rings of 1–2 total hetero atoms which can contain, besides the N-atom, also O or S or another N. Examples include pyrrolo, pyrrolino, thiazolino, oxazolino, pyrrolidino, piperidino, piperazino, N-methylpiperazino, or morpholino.

It is known that certain sites in the central nervous system of vertebrates exhibit a high specific affinity for binding 1,4- and 1,5-benzodiazepines [Squires, R. F. and Braestrup, C., Nature (London) 266:734 (1977)]. The sites are called benzodiazepine receptors.

It has been found that the 5H-pyrimido[5,4-b]-indoles of this invention, although differing in chemical structure from benzodiazepines, surprisingly show strong affinity for binding to benzodiazepine receptors, in that they displace radioactively labeled flunitrazepam from benzodiazepine receptors.

The compounds of this invention possess a spectrum of activity similar to that of flunitrazepam. They can be formulated into psychopharmaceutical preparations, for example for oral and/or parenteral administration to mammals, including humans, and can be administered in the same way as flunitrazepam.

In view of their ability to bind benzodiazepine receptors, the compounds of this invention are useful to treat diseases of the central nervous system, e.g., insomnia, anxiety, unrest, fear, epilepsy and seizures of various origins, e.g., febrile or toxic. They are particularly useful as tranquilizers in mammals including humans, at daily dosages of 1–200, preferably 1–50 mg/day, using regimens analogous to that used with the conventional tranquilizer Valium.

Suitable auxiliary agents for formulation are physiologically compatible, organic and inorganic excipients inert with respect to the compounds of this invention.

Examples of excipients include water, saline solutions, alcohols, polyethylene glycols, polyhydroxyethoxylated castor oil, gelatin, lactose, amylose, magnesium stearate, talc, silicic acid, fatty acid mono- and diglycerides, pentaerythritol fatty acid esters, hydroxymethylcellulose, and polyvinylpyrrolidone.

The pharmaceutical preparations can be sterilized and/or combined with auxiliary materials, such as lubricants, preservatives, stabilizers, wetting agents, emulsifiers, buffers, and colorants.

Especially suitable for parenteral administration are injection solutions of suspensions, particularly aqueous solutions of the active compounds in polyhydroxyethoxylated castor oil.

Especially suitable for oral administration are tablets, dragees, or capsules with talc and/or with a hydrocarbon vehicle or binder, e.g., lactose, cornstarch, or potato starch. The administration can also be in liquid form, e.g. as an elixir to which a sweetener has been added, if desired.

The compounds of this invention are usually incorporated into a physiologically compatible excipient in a dosage unit of 0.05–10 mg of active agent.

The compounds according to this invention are usually utilized in a dose of 0.1–300 mg/day, preferably 1–30 mg/day, for all of the above indications.

Dosages for a given host for a given indication can be determined, e.g., by customary comparison of the activities of the subject compound and of a known agent by means of an appropriate, conventional pharmacological protocol.

The compounds of general Formula I are prepared according to classical methods of organic chemistry. For example, processes for the preparation of compounds of Formula I, involve the following steps:

(a) from corresponding 5-R' compounds of Formula II

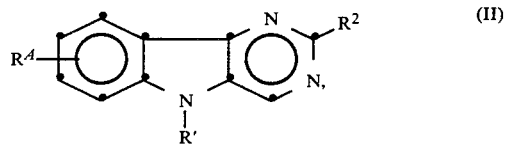

wherein
R' is tosyl, phenylsulfonyl, or methoxyphenylsulfonyl, and $R^2$ and $R^A$ are as defined for Formula I,
R' is split off with a strong base and any acids that may have been produced by hydrolysis are optionally esterified, and the thus-obtained ester is, if desired, conventionally interesterified or reacted with hydrazine; the resultant hydrazide is optionally converted into the azide, and the carboxylic acid azide is thermally decomposed by a Curtius reaction and converted by hydrolysis into the amine; the amine or hydrazide is, if desired, alkylated, alkenylated, aralkylated, arylated, reacted with 2,5-dimethoxytetrahydrofuran, 1,4-dibromobutane, or 1,5-dibromopentane; or the amine is reacted in a Sandmeyer reaction with dilute sulfuric acid, with hydrohalic acid in the presence of copper(I) halide, with $R^IOH$ or $(R^I)_2S_2$ wherein $R^I$ has the above-indicated meanings; and, if desired, an $R^IS$ compound obtained with $(R^I)_2S_2$ is oxidized to the $R^ISO$ or $R^ISO_2$ compound; or an $R^IO$ compound is subjected to ether cleavage and optionally the OH compound is again esterified; or (b) a compound of Formula III

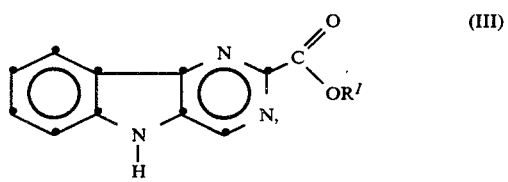

wherein $R^I$ is as defined for Formula I, is nitrated in a conventional way and, if desired, the thus-obtained nitro compounds are reduced to the corresponding amino compounds and optionally the amino compounds are halogenated in the o-position, or the amine is alkylated, alkenylated, aralkylated, arylated, reacted with 2,5-dimethoxytetrahydrofuran, 1,4-dibromobutane, 1,5-dibromopentane, or the amine, optionally after halogenation in the o-position, is reacted in a Sandmeyer reaction with dilute sulfuric acid, with hydrohalic acid in the presence of copper(I) halide, with $R^IOH$ or $(R^I)_2S_2$ wherein $R^I$ has the meanings given above; or is conventionally halogenated and the resultant halogenation product is optionally reacted to form the $(RO)_2OP$, $R^IO$, or $R^IOCO$ compound and, if desired, the $R^IOCO$ compound is interesterified, saponified, or amidated, and optionally the hydroxycarbonyl compound is reacted to the halocarbonyl compound, the halocarbonyl compound is optionally reacted with an amine of the formula $R^{II}R^{III}NH$ or an alcohol of the formula $R^IOH$; or is conventionally sulfonated and, if desired, the thus-obtained chlorosulfonyl compounds are reacted with an amine of the formula $R^{II}R^{III}NH$, (c) a compound of Formula IV

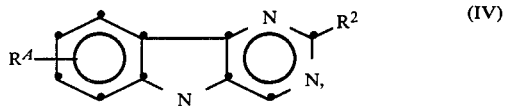

wherein
$R^A$ has the meaning of $NR^{II}R^{III}$ or $COOR^I$,
$R^2$ has the meaning of $COOR^I$, wherein $R^I$, $R^{II}$ and $R^{III}$ are as defined above, is hydrolysed and than the free acid is reacted with a compound having the Formula

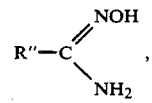

wherein R' is lower alkyl with up to 3 carbon atoms, to form a compound of Formula I wherein R'', $R^A$ and/or $R^2$ has the meaning of

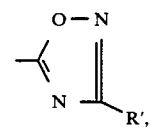

wherein R' has the meaning defined above.

Thus, R' is split off conventionally from 5-R' compounds of Formula II. Depending on the desired meaning of $R^2$ and $R^A$ in the final product of Formula I, the substituents R² and R⁴ that are present can be conventionally modified, or one or several substituents R⁴ can be conventionally introduced and, if desired, subsequently modified.

The splitting off of group R' according to process (a) can be effected with strong bases. Suitable bases include, for example, alkali metal alcoholates and alkali metal hydroxides in an alcoholic solution. The reaction is accomplished by prolonged standing at room temperature or by heating under reflux.

In the presence of an ester group —COOR$^I$ and with alkaline treatment in boiling heat, the ester is partially hydrolyzed and, if desired, can be reconstituted by treatment with the corresponding alcohol in the presence of an acid.

An optional interesterification of the ester group likewise can be effected according to known methods with an alcohol R$^I$OH, for example in the presence of an acidic catalyst, such as sulfuric acid, p-toluenesulfonic acid, HCl, or CuCl₂ in boiling heat.

The ester group can optionally be converted with hydrazine into the hydrazide in a manner known per se, and the hydrazide can be converted into the azide. The carboxylic acid azide can subsequently be subjected to Curtius decomposition wherein the urethanes, formed initially with an alcohol, can be converted into the amines by acidic or alkaline hydrolysis.

Amino or hydrazino compounds can, if desired, be subsequently conventionally alkylated, alkenylated, aralkylated, arylated or reacted, for example with 2,5-dimethoxytetrahydrofuran in the presence of an acid or with 1,4-dibromobutane or 1,5-dibromopentane in the presence of a base.

The conversion of the amino compounds into the corresponding hydroxy, halogen, R$^I$O and R$^I$S compounds also takes place conventionally, for example in accordance with the Sandmeyer reaction wherein the diazotized product is reacted directly with dilute sulfuric acid, with hydrohalic acid in the presence of copper(I) halide, with R$^I$OH, or (R$^I$)₂S₂ at elevated temperatures. R$^I$S compounds can, if desired, be subsequently oxidized to R$^I$SO and R$^I$SO₂ compounds. Suitable oxidizing agents include, for example, organic peracids, such as performic acid, peracetic acid, perbenzoic acid, m-chloroperbenzoic acid, monoperphthalic acid, but also inorganic peroxides, such as hydrogen peroxide, dissolved in water or in dilute organic acids. By selection of the reaction conditions as known from the literature, the oxidation potential can be correspondingly set, and the reaction can be conventionally and readily regulated for producing the sulfoxides or sulfones.

Ether (R$^I$O) compounds of Formula I can be conventionally hydrolyzed to the hydroxy (R$^I$O) compounds. Hydrolysis is preferably effected with Lewis acids, e.g., boron tribromide in methylene chloride, or hydrobromic acid in water, by prolonged standing at room temperature or by heating at reflux temperature.

An optionally desired etherification of the hydroxy group in the compounds of Formula I is likewise conducted according to methods known per se. For this purpose, the hydroxy compound can be reacted, for example, in the presence of an alkali metal carbonate in a polar solvent, e.g., acetonitrile, dimethylformamide, or 1-methyl-2-pyrrolidone, with an alkyl, alkenyl, cycloalkyl, arylalkyl, or aryl halogenide.

Nitration of the compounds of Formula III according to process (b) is likewise conducted according to methods known per se. Thus, the starting material can be reacted at temperatures of 0° to 100° C. with concentrated nitric acid or with a mixture of concentrated nitric acid and concentrated sulfuric acid. The acid utilized in the nitration serves as the reagent as well as the solvent. Nitro groups, preferably in the 6- and 8-positions, are introduced with 100% nitric acid with the addition of concentrated sulfuric acid; 65% nitric acid is used to introduce one nitro group, preferably in the 6- or 8-position.

The optionally following reduction of the resultant nitro compound to the corresponding amino compound also takes place according to conventional methods.

A preferred method is the reduction with hydrogen in the presence of metallic catalysts, such as Raney nickel, platinum in finely divided form, or palladium on a suitable support, such as carbon or lime under normal pressure and at room temperature. However, it is also possible to employ hydrogen in the nascent state, for example by means of zinc/hydrochloric acid.

A thus-obtained 8-amino compound can be halogenated in the 9-position with hydrohalic acid in an oxidizing solvent, such as dimethyl sulfoxide. With hydrobromic acid, for example, the 8-amino-9-bromo compound is obtained from the 8-amino compound. If desired, the amino group can subsequently be eliminated in a manner per se.

In order to produce a compound of Formula I, wherein R⁴ and/or R² has the meaning of the oxadiazol group, a compound of Formula IV is hydrolysed to give the free carboxylic acid derivative. The free acid is reacted under condensation with an amide oxime of the formula

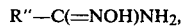
R''—C(=NOH)NH₂, wherein R'' is a lower alkyl group with up to 3 carbon atoms, in a solvent of which the boiling point is over 100° C. and which is inert to the reactants by refluxing the reaction mixture. Suitable solvents are, e.g., toluene and dimethylformamide. A preferred method of condensation is the activation of the free carboxylic acid prior to condensation. It is possible to form the corresponding mixed anhydride, an activated ester or the acid chloride. A preferred method is the activation reaction with a mixture of imidazole and thionyl chloride in an aprotic solvent like dioxane, tetrahydrofurane, dimethylformamide or N-methyl pyrrolidone at temperatures between 0° and 50° C., preferable at room temperature.

In order to produce compounds of Formula I with a substituted amino group NR$^{II}$R$^{III}$, corresponding 5H-pyrimido[5,4-b]indole-2-carboxylic acid esters, substituted with an amino group (R⁴), are conventionally reacted in a suitable solvent in the presence of a base with an alkyl, alkenyl, cycloalkyl, aralkyl, or aryl halogenide, tosylate, or mesylate at temperatures in the range from room temperature to the boiling point of the reaction mixture, preferably at 20°–120° C.

Suitable for the reaction are actually all protonic and aprotic solvents, insofar as they are inert with respect to the reactants. Examples include aliphatic alcohols, such as methanol, ethanol, and propanol, ketones, such as acetone and methyl isobutyl ketone, ethers, such as glycol dimethyl ether and diethyl ether, cyclic ethers, such as tetrahydrofuran and dioxane, as well as solvents, such as dimethylformamide, dimethylacetamide, and N-methylpyrrolidone.

Suitable bases are actually all strong organic bases, such as triethylamine, 4-dimethylaminopyridine, ethylenediisopropylamine, diazabicycloundecane, -nonane, and -octane. However, it is also possible to use an alkali metal carbonate, such as sodium or potassium carbonate, but also alcoholates, such as potassium tert-butylate. In order to produce ring-closed $NR^{II}R^{III}$ compounds, the corresponding amino compounds are treated with dihaloalkane or dihaloalkene. A suitable halogen is chlorine, bromine, or iodine; in case of chlorine, the addition of a coppper(I) halide, such as copper(I) iodide, is advantageous.

With the use of 2,5-dimethoxytetrahydrofuran, the corresponding pyrrolyl compound is obtained from the amino compound in the presence of an acid.

The conversion of the amino group $R^4$ into the corresponding hydroxy, halogen, $R^IO$, and $R^ISO_n$ compounds again takes place conventionally with the aid of the Sandmeyer reaction.

The halogenation of the compounds of Formula III according to process (b) is effected according to known methods. For this purpose, the starting material is dissolved in an inert solvent and reacted with the corresponding halogen, such as chlorine or bromine, if desired in the presence of an alkaline catalyst, at temperatures of 0° to 50° C. Examples of inert solvents include chlorinated hydrocarbons, such as methylene chloride, chloroform, dichloroethylene, etc. Alkaline catalysts suitable in this connection are pyridine and substituted pyridines, such as 4-dimethylaminopyridine. An alkaline catalyst is dispensable in the chlorination reaction.

For the introduction of iodine, not only elemental iodine can be utilized, but also a mixture of iodine and iodic acid; in this connection, the reaction is preferably conducted in glacial acetic acid at 80°–100° C. with protonic catalysis.

The optionally following reaction of the iodine compound with dialkyl phosphite is carried out in the presence of a soluble noble metal complex, e.g. palladium tetrakis(triphenylphosphine) and of a base, e.g. triethylamine, pyridine, or 4-dimethylaminopyridine, in an aprotic polar solvent at temperatures of 20°–140° C. Suitable aprotic polar solvents include, for example, hexamethylphosphoric triamide and N-methylpyrrolidone.

The halogen compound, especially the 8-iodo compound, can furthermore be carbonylated with palladium(II) acetate and carbon monoxide in alcohols, such as, for example, benzyl alcohol, and in the presence of a tertiary amine, e.g. triethylamine, tributylamine, or pyridine. The thus-obtained 8-benzyloxycarbonyl compound can then be conventionally saponified, interesterified, or made to react with an amine of the formula $R^{II}R^{III}NH$. The 8-benzyloxycarbonyl group can, however, also be selectively debenzylated by hydrogenation.

For interesterification purposes, the existing ester is heated with an alcohol $R^IOH$ in the presence of catalytic amounts of $R^IONa$ or NaH for 3–6 hours to temperatures of 60° to 120° C. Optionally, interesterification with the alcohol $R^IOH$ can also be effected in the presence of an acidic catalyst, such as p-toluenesulfonic acid, HCl, or $CuCl_2$.

The free 8-hydroxycarbonyl compound can be conventionally converted into the halocarbonyl compound, for example with thionyl chloride into the chlorocarbonyl compound.

The halocarbonyl compound, in turn, can be conventionally reacted with an amine of the formula $R^{II}R^{III}NH$ or with an alcohol of the formula $R^IOH$.

Sulfochlorination of the compounds of Formula III according to process (b) takes place by means of conventional methods. For this purpose, the starting material can be combined with chlorosulfonic acid, if desired in an inert solvent, such as methylene chloride or chloroform. In order to prepare corresponding aminosulfonic acid derivatives, the resultant product is made to react with an amine of the formula $R^{II}R^{III}NH$ and then heated to 60°–100° C.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention.

The starting materials of formulae II and III are all known compounds and/or conventionally preparable using known reactions starting from known or readily preparable starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

2-Methyl-5H-pyrimido[5,4-b]indole (a) At room temperature, 4.5 g of 3-acetylamino-1-tosylindole-2-carbonitrile is hydrogenated for several hours in 600 ml of ammonia-saturated ethanol with the addition of 8 g of Raney nickel under a hydrogen pressure of 70 bar. The catalyst is then suctioned off, and the filtrate is evaporated as exhaustively as possible under vacuum.

(b) The residue (2-methyl-5-tosyl-5H-pyrimido-[5,4-b]indole) is taken up in 100 ml of ethanol and combined with a solution of 1.4 g of sodium in 90 ml of ethanol. The mixture is refluxed for 2 hours. Then the mixture is poured into an aqueous sodium dihydrogen phosphate solution. The aqueous phase is extracted by shaking with methylene chloride. The methylene chloride extracts are washed with saturated sodium chloride solution, dried, and evaporated. The residue is chromatographed with a mixture of 10 parts of methylene chloride and one part of methanol on silica gel, thus obtaining 0.13 g of 2-methyl-5H-pyrimido[5,4-b]indole, mp 240°–242° C.

3-Acetylamino-1-tosylindole-2-carbonitrile, needed as the starting material, is prepared as follows:

One gram of 3-amino-1-tosylindole-2-carbonitrile is heated in 2 ml of pyridine with 0.4 ml of acetic anhydride for 10 hours to 80° C. The crystals precipitating upon cooling are suctioned off and washed with methanol.

Yield: 0.81 g of 3-acetylamino-1-tosylindole-2-carbonitrile, mp 181°–183° C.

EXAMPLE 2

5H-Pyrimido[5,4-b]indole-2-carboxylic Acid

In an argon atmosphere, a solution of 0.355 g of sodium in 35 ml of ethanol is added dropwise to a solution of 2.36 g of 5-tosyl-5H-pyrimido[5,4-b]indole-2-carboxylic acid ethyl ester in 70 ml of ethanol. The mixture is then refluxed for one-half hour. The precipitate obtained in crystallized form upon cooling is vacuum-filtered and recrystallized from water.

Yield: 0.12 g of 5H-pyrimido[5,4-b]indole-2-carboxylic acid, mp 265°–268° C.

By evaporation and extraction with ethyl acetate, 0.3 g of 5H-pyrimido[5,4-b]indole-2-carboxylic acid ethyl ester (see Example 3) is isolated from the ethanol mother liquor.

The ethyl ester of 5-tosyl-5H-pyrimido[5,4-b]indole-2-carboxylic acid required as the starting material is produced as follows:

(a) Under stirring and ice cooling, 10 ml of oxalic acid ethyl ester chloride is added dropwise gradually to 5 g of 3-amino-1-tosylindole-2-carbonitrile. The lumpy reaction mixture is finely distributed by agitation with ethanol and suctioned off. The yield is 4.8 g of oxalic acid monoethyl ester mono(2-cyano-1-tosyl-3-indolyl)amide, mp 156°–157° C.

(b) With the addition of 6 g of Raney nickel, 3.2 g of oxalic acid monoethyl ester mono(2-cyano-1-tosyl-3-indolyl)amide is hydrogenated at room temperature under normal pressure in 480 ml of ethanol. The duration of hydrogen absorption is about 20 hours.

The solution, filtered off from the catalyst, is evaporated, and the residue is chromatographed with a mixture of equal parts of toluene and ethyl acetate over silica gel, thus producing 0.4 g of 5-tosyl-5H-pyrimido[5,4-b]indole-2-carboxylic acid ethyl ester and 0.2 g of 1,4-dihydro-5-tosyl-5H-pyrimido[5,4-b]indole-2-carboxylic acid ethyl ester, mp 175°–178° C.

(c) Under argon, 10 g of 1,4-dihydro-5-tosyl-5H-pyrimido[5,4-b]indole-2-carboxylic acid ethyl ester is refluxed for 10 hours in 200 ml of xylene with 5 g of 10% Pd-carbon. The filtrate is then removed from the palladium-carbon by evaporation, the evaporation residue yielding, after recrystallization from an ethyl acetate/ether mixture, 5 g of 5-tosyl-5H-pyrimido[5,4-b]indole-2-carboxylic acid ethyl ester, mp 187°–189° C.

EXAMPLE 3

5H-Pyrimido[5,4-b]indole-2-carboxylic Acid Ethyl Ester

A suspension is prepared from 12 g of 5H-pyrimido[5,4-b]indole-2-carboxylic acid (Example 2) in 50 ml of ethanol, and the suspension is refluxed in an argon atmosphere for 8 hours with the addition of 1.1 ml of concentrated sulfuric acid. The reaction mixture is thereafter concentrated and the residue taken up in methylene chloride/water. The methylene chloride phase is washed with water, dried, and evaporated. The residue is recrystallized from ethanol.

Yield: 1.1 g of 5H-pyrimido[5,4-b]indole-2-carboxylic acid ethyl ester, mp 244°–246° C.

EXAMPLE 4

5H-Pyrimido[5,4-b]indole-2-carboxylic Acid n-Propyl Ester

In 5 ml of n-propanol, 0.5 g of 5H-pyrimido[5,4-b]indole-2-carboxylic acid ethyl ester (Example 3) is refluxed with a spatula tip of p-toluenesulfonic acid for 45 hours. The reaction mixture is then evaporated and, while treating with active carbon, recrystallized from isopropanol.

Yield: 0.15 g of 5H-pyrimido[5,4-b]indole-2-carboxylic acid n-propyl ester, mp 222°–224° C.

EXAMPLE 5

5H-Pyrimido[5,4-b]indole-2-carboxylic Acid Hydrazide

Under argon, 0.5 g of 5H-pyrimido[5,4-b]indole-2-carboxylic acid ethyl ester (Example 3) is refluxed in 25 ml of ethanol with 0.5 ml of hydrazine hydrate for 2 hours. After standing overnight, 0.5 g of 5H-pyrimido[5,4-b]indole-2-carboxylic acid hydrazide is suctioned off from the reaction mixture, mp >340° C.

EXAMPLE 6

5H-Pyrimido[5,4-b]indole-2-carboxylic Acid Azide

Under heating, 0.3 g of 5H-pyrimido[5,4-b]indole-2-carboxylic acid hydrazide (Example 5) is dissolved in a mixture of 6 ml of glacial acetic acid and 2.4 ml of water. Then, a solution of 0.33 g of sodium nitrite in 1 ml of water is added gradually thereto at 0° C. After adding the nitrite, the mixture is stirred for another 4 hours at 0° C., thereafter rendered alkaline with sodium carbonate solution, and the thus-crystallized 5H-pyrimido[5,4-b]indole-2-carboxylic acid azide is vacuum-filtered. The yield is 0.3 g.

EXAMPLE 7

5H-Pyrimido[5,4-b]indole-2-amine 0.1 g of 5H-pyrimido[5,4-b]indole-2-carboxylic acid azide (Example 6) is refluxed in 3 ml of 60% strength acetic acid for 3 hours. The filtered reaction solution is rendered alkaline with 1N sodium hydroxide solution. The thus-precipitating crystals are suctioned off. Then the crystallized product is taken up in a mixture of ethyl acetate and methylene chloride, the solution is washed with water, dried, and evaporated. There remains 0.04 g of 5H-pyrimido[5,4-b]indole-2-amine, mp 258°–260° C.

EXAMPLE 8

6,8-Dinitro-5H-pyrimido[5,4-b]indole-2-carboxylic Acid

A solution is prepared from 0.1 g of 5H-pyrimido[5,4-b]indole-2-carboxylic acid (Example 2) in 1 ml of 100% strength nitric acid and 0.5 ml of concentrated sulfuric acid, and the solution is stirred for one hour at room temperature as well as for one hour at 60° C. After allowing the reaction mixture to stand for 2 days, it is poured on ice, the thus-precipitated crystals are dissolved in sodium hydroxide solution, and reprecipitated from the solution by acidifying with hydrochloric acid. The yield is 0.05 g of 6,8-dinitro-5H-pyrimido[5,4-b]indole-2-carboxylic acid, mp 269°–272° C.

EXAMPLE 9

6,8-Dinitro-5H-pyrimido[5,4-b]indole-2-carboxylic Acid Ethyl Ester

Under argon, 0.2 g of 6,8-dinitro-5H-pyrimido[5,4-b]indole-2-carboxylic acid (Example 8) is refluxed in 20 ml of ethanol with the addition of 1 ml of concentrated sulfuric acid for 8 hours. Subsequently the solution is concentrated to half the quantity and dissolved in methylene chloride. The solution is washed first with water, then with sodium bicarbonate solution, and finally again with water, dried, and concentrated, yielding 0.18 g of 6,8-dinitro-5H-pyrimido[5,4-b]indole-2-carboxylic acid ethyl ester, mp 295°–299° C.

EXAMPLE 10

6- and 8-Nitro-5H-pyrimido[5,4-b]indole-2-carboxylic Acid Ethyl Esters 0.325 g of 5H-pyrimido[5,4-b]indole-2-carboxylic acid ethyl ester (Example 3) is stirred in 6 ml of 65% strength nitric acid for 15 minutes at room temperature, then for one hour at 70° C. Thereafter the reaction mixture is poured into ice water and extracted with ethyl acetate. The combined ethyl acetate extracts are evaporated; the evaporation residue is chromatographed on silica gel with a mixture of equal parts of methylene chloride and acetone, thus obtaining 0.012 g of 6-nitro-5H-pyrimido[5,4-b]indole-2-carboxylic acid ethyl ester (mp 318°–325° C.) and 0.023 g of 8-nitro-5H-pyrimido[5,4-b]indole-2-carboxylic acid ethyl ester, mp 304°–306° C.

EXAMPLE 11

8-Amino-5H-pyrimido[5,4-b]indole-2-carboxylic Acid Ethyl Ester 1.5 g of 8-nitro-5H-pyrimido[5,4-b]indole-2-carboxylic acid ethyl ester (Example 10) is hydrogenated in 90 ml of a mixture of equal parts of tetrahydrofuran and methanol at normal temperature under a hydrogen pressure of 70 bar, with the addition of 0.21 g of 10% palladiumcarbon. The solution, freed of catalyst, is evaporated, the residue is taken up in ethyl acetate and a small amount of ethanol, filtered, and evaporated to ¾ its quantity, thus precipitating 0.400 g of 8-amino-5H-pyrimido[5,4-b]indole-2-carboxylic acid ethyl ester, mp 256°–258° C.

EXAMPLE 12

8-Diallylamino-5H-pyrimido[5,4-b]indole-2-carboxylic Acid Ethyl Ester

Under argon, 0.4 g of 8-amino-5H-pyrimido[5,4-b]indole-2-carboxylic acid ethyl ester (Example 11) is agitated in 8 ml of ethanol with 0.16 ml of diazabicycloundecane and 0.25 ml of allyl bromide for 5 hours at 50°–60° C. The reaction solution is subsequently evaporated, and the residue is taken up in ethyl acetate. This solution is washed first with water, then with sodium bicarbonate solution, and finally again with water, dried with sodium sulfate, and concentrated, thus obtaining 0.18 g of 8-diallylamino-5H-pyrimido[5,4-b]indole-2-carboxylic acid ethyl ester, mp 188°–190° C.

EXAMPLE 13

8-Iodo-5H-pyrimido[5,4-b]indole-2-carboxylic Acid Ethyl Ester 2 g of 5H-pyrimido[5,4-b]indole-2-carboxylic acid ethyl ester (Example 3) in 20 ml of glacial acetic acid is combined with 0.5 ml of water, 0.12 ml of concentrated sulfuric acid, 336 mg of iodic acid, and 878 mg of iodine and agitated for 2.5 hours at 90° C. After concentrating the reaction mixture, the latter is combined with 50 ml of water, gently made alkaline with ammonia, and suctioned off, thus obtaining 2.81 g of 8-iodo-5H-pyrimido[5,4-b]indole-2-carboxylic acid ethyl ester, mp 264°–266° C. under decomposition.

EXAMPLE 14

8-Bromo-5H-pyrimido[5,4-b]indole-2-carboxylic Acid Ethyl Ester

A solution is prepared from 1.15 g of 5H-pyrimido[5,4-b]indole-2-carboxylic acid ethyl ester (Example 3) in 50 ml of chloroform and 5.3 ml of pyridine and combined dropwise with 1 g (0.33 ml) of bromine in 10 ml of chloroform at room temperature. After 6 hours of agitation, the mixture is concentrated, taken up in 30 ml of water, made alkaline with ammonia, layered over with ethyl acetate, and then shaken and suctioned off. The thus-obtained residue is 0.86 g of 8-bromo-5H-pyrimido[5,4-b]indole-2-carboxylic acid ethyl ester, mp 286°–290° C. (under decomposition).

EXAMPLE 15

8-N,N-Dimethylsulfonamido-5H-pyrimido[5,4-b]indole-2-carboxylic Acid Ethyl Ester 486 mg of 5H-pyrimido[5,4-b]indole-2-carboxylic acid ethyl ester (Example 3) is gradually introduced into 2 ml of chlorosulfonic acid at 4° C. Subsequently the mixture is gently heated to 80° C. and further agitated for 30 minutes at this temperature. After cooling, the mixture is dropped into 25 ml of ice (violent reaction). Then the mixture is neutralized with 40% aqueous dimethylamine solution, vacuum-filtered from the insoluble residue, and the filtrate is extracted three times with respectively 50 ml of ethyl acetate. The organic phase is washed once with saturated sodium chloride solution, dried with calcium sulfate, filtered, and concentrated. The residue is chromatographed over silica gel with methylene chloride/ethanol=10:1 as the eluent, thus obtaining 105 mg of 8-N,N-dimethylsulfonamido-5H-pyrimido[5,4-b]indole-2-carboxylic acid ethyl ester, mp 299°–301° C. under decomposition.

EXAMPLE 16

8-Diethylphosphoryl-5H-pyrimido[5,4-b]indole-2-carboxylic Acid Ethyl Ester 510 mg of 8-iodo-5H-pyrimido[5,4-b]indole-2-carboxylic acid ethyl ester (Example 13) is added to a mixture of 0.22 ml of diethyl phosphite, 0.22 ml of triethylamine, 120 mg of palladium tetrakis(triphenylphosphine) in 25 ml of N-methylpyrrolidone, and stirred under argon at 90° C. for 4 hours. After adding 0.22 ml of diethyl phosphite, 0.22 ml of triethylamine, and 120 mg of palladium tetrakis(triphenylphosphine), the mixture is once again heated for 3 hours to 90° C. After concentration at a bath temperature of 80° C. (oil pump), the residue is chromatographed over silica gel with the use of methylene chloride/ethanol=10:1 as the eluent. Recrystallization of the corresponding fractions from ethyl acetate/diisopropyl ether yields 131 mg of 8-diethylphosphoryl-5H-pyrimido[5,4-b]indole-2-carboxylic acid ethyl ester, mp 195°–197° C.

EXAMPLE 17

8-Benzyloxycarbonyl-5H-pyrimido[5,4-b]indole-2-carboxylic Acid Ethyl Ester 700 mg of 8-iodo-5H-pyrimido[5,4-b]indole-2-carboxylic acid ethyl ester (Example 13) is heated in 12 ml of benzyl alcohol with 0.5 ml of tri-n-butylamine under a carbon monoxide atmosphere to 110° C., then combined with 20 mg of palladium(II) acetate, and stirred for 3 hours at 110° C. After removing the benzyl alcohol by distillation under an oil pump vacuum, the mixture is dissolved in dimethylformamide and ethanol and suctioned off from the catalyst. The mixture is then concentrated, extracted by stirring with ethanol, and suctioned off, yielding 501 mg of 8-benzyloxycarbonyl-5H-pyrimido[5,4-b]indole-2-carboxylic acid ethyl ester, mp 271°–272° C.

EXAMPLE 18

8-Hydroxycarbonyl-5H-pyrimido[5,4-b]indole-2-carboxylic Acid Ethyl Ester

At room temperature, 1.18 g of 8-benzyloxycarbonyl-5H-pyrimido[5,4-b]indole-2-carboxylic acid ethyl ester (Example 17) is hydrogenated under a hydrogen pressure of one bar for 2 hours in a mixture of 60 ml of N-methylpyrrolidone, 20 ml of methanol, and 10 ml of 1N hydrochloric acid with 498 mg of palladium on carbon (10%). After vacuum-filtering over kieselguhr, the mixture is concentrated. The residue is extracted in a mixture of ethyl acetate, ethanol, and petroleum ether, thus obtaining 900 mg of 8-hydroxycarbonyl-5H-pyrimido[5,4-b]indole-2-carboxylic acid ethyl ester in the form of a hydrochloride.

EXAMPLE 19

8-Chlorocarbonyl-5H-pyrimido[5,4-b]indole-2-carboxylic Acid Ethyl Ester 184 mg of 8-hydroxycarbonyl-5H-pyrimido[5,4-b]indole-2-carboxylic acid ethyl ester (Example 18) is refluxed for 3 hours in 5 ml of thionyl chloride with one drop of dimethylformamide. After concentration, the mixture is further reacted without any purification.

EXAMPLE 20

8-N,N-Dimethylcarbamoyl-5H-pyrimido[5,4-b]indole-2-carboxylic Acid Ethyl Ester 180 mg of 8-chlorocarbonyl-5H-pyrimido[5,4-b]indole-2-carboxylic acid ethyl ester (Example 19) is suspended in 5 ml of absolute tetrahydrofuran and, at 4° C., combined dropwise with a 1-molar solution of dimethylamine in tetrahydrofuran to pH 8. Subsequently the mixture is stirred for 2 hours at 4° C. After pouring the mixture into water, the mixture is vacuum-filtered. The residue is extracted by stirring in ethyl acetate/ethanol, thus obtaining 90 mg of 8-N,N-dimethylcarbamoyl-5H-pyrimido[5,4-b]indole-2-carboxylic acid ethyl ester, mp 289°–292° C. (under decomposition).

EXAMPLE 21

8-N,N-Diallylcarbamoyl-5H-pyrimido[5,4-b]indole-2-carboxylic Acid Ethyl Ester

The title compound is produced analogously to Example 20.

EXAMPLE 22

8-Ethoxycarbonyl-5H-pyrimido[5,4-b]indole-2-carboxylic Acid Ethyl Ester

A suspension of 150 mg of 8-chlorocarbonyl-5H-pyrimido[5,4-b]indole-2-carboxylic acid ethyl ester (Example 19) in 5 ml of tetrahydrofuran is combined with a solution of triethylamine in ethanol at 4° C. until a pH of 8 is attained. The mixture is then stirred for 2 hours at room temperature and evaporated. After distribution in ethyl acetate/dilute ammonia solution, the organic phase is separated, dried, filtered, and concentrated. After chromatography over silica gel with methylene chloride/ethanol=10:1 as the eluent, 70 mg of 8-ethoxycarbonyl-5H-pyrimido[5,4-b]indole-2-carboxylic acid ethyl ester is obtained.

EXAMPLE 23

8-Methylthio-5H-pyrimido[5,4-b]indole-2-carboxylic Acid Ethyl Ester 400 mg of 8-amino-5H-pyrimido[5,4-b]indole-2-carboxylic acid ethyl ester (Example 11) is heated in 4.8 ml of dimethyl disulfide under argon to 60° C. The mixture is then combined with 2.8 ml of isoamyl nitrite and heated for one hour to 80° C. After evaporation, the mixture is chromatographed over silica gel with methylene chloride/ethanol=10:1 as the eluent. Recrystallization of the corresponding fractions yields 130 mg of 8-methylthio-5H-pyrimido[5,4-b]indole-2-carboxylic acid ethyl ester, mp 265°–266° C.

EXAMPLE 24

8-Amino-9-bromo-5H-pyrimido[5,4-b]indole-2-carboxylic Acid Ethyl Ester

One gram of 8-amino-5H-pyrimido[5,4-b]indole-2-carboxylic acid ethyl ester (Example 11) is combined with such an amount of dimethyl sulfoxide that a clear solution is produced. Then, at 0°–5° C., the same amount of 48% aqueous hydrobromic acid is added dropwise and the mixture stirred thereafter for another 2 hours at this temperature, thus obtaining the ethyl ester of 8-amino-9-bromo-5H-pyrimido[5,4-b]indole-2-carboxylic acid.

EXAMPLE 25

9-Bromo-5H-pyrimido[5,4-b]indole-2-carboxylic Acid Ethyl Ester

A suspension of 1 g of 8-amino-9-bromo-5H-pyrimido[5,4-b]indole-2-carboxylic acid ethyl ester in 70 ml of ethanol is combined with 1.8 ml of isoamyl nitrite. The mixture is refluxed for one hour and then concentrated. Yield: 0.2 g of 9-bromo-5H-pyrimido[5,4-b]indole-2-carboxylic acid ethyl ester.

EXAMPLE 26

2-Bromo-5H-pyrimido[5,4-b]indole

A solution is prepared from 2 g of 2-amino-5H-pyrimido[5,4-b]indole (Example 7) in 25 ml of 48% strength hydrobromic acid and combined at 0° C. with 6 ml of a 2N sodium nitrite solution. The mixture is stirred into a solution of 2.1 g of copper(I) bromide in 20 ml of 24% strength hydrobromic acid. The mixture is then stirred for 20 minutes at 0° C., then briefly heated on a steam bath. The cooled-off reaction mixture is extracted with a mixture of 9 parts of ethyl acetate and one part of ethanol. The residue is evaporated and chromatographed on silica gel with a mixture of 20 parts of methylene chloride and one part of methanol, thus obtaining 0.2 g of 2-bromo-5H-pyrimido[5,4-b]indole.

EXAMPLE 27

2-Chloro-5H-pyrimido[5,4-b]indole

The title compound is produced in analogy to Example 26 with hydrochloric acid.

EXAMPLE 28

9-Methoxy-5H-pyrimido[5,4-b]indole-2-carboxylic Acid Ethyl Ester

The compound is prepared, starting with 3-amino-4-methoxy-1-tosylindole-2-carbonitrile, in accordance with the process described in Examples 2 and 3.

The 3-amino-4-methoxy-1-tosylindole-2-carbonitrile, needed as the starting material, is obtained from 2-amino-6-methoxybenzonitrile analogously to the synthesis of 3-amino-1-tosylindole-2-carbonitrile known from the literature [Kenneth Clarke, William Richard Fox, and Richard M. Scrowston: J. Chem. Res. 1980 (2): 833-847].

The 7-methoxy-5H-pyrimido[5,4-b]indole-2-carboxylic acid ethyl ester is produced analogously, but starting with 2-amino-4-methoxybenzonitrile.

EXAMPLE 29

9-Hydroxy-5H-pyrimido[5,4-b]indole-2-carboxylic Acid Ethyl Ester

A suspension of 0.52 g of 9-methoxy-5H-pyrimido[5,4-b]indole-2-carboxylic acid ethyl ester (Example 28) in 50 ml of methylene chloride is combined with 4 ml of a 1-molar solution of boron tribromide in methylene chloride. The reaction mixture is stirred overnight under argon. Then 2 ml of ethanol is added dropwise to the reaction mixture under cooling with ice water. After the addition of 500 ml of ether, the precipitate, consisting of 9-hydroxy-5H-pyrimido[5,4-b]indole-2-carboxylic acid ethyl ester, is suctioned off.

EXAMPLE 30

9-Benzyloxy-5H-pyrimido[5,4-b]indole-2-carboxylic Acid Ethyl Ester

Under an argon atmosphere, a solution of 0.2 g of 9-hydroxy-5H-pyrimido[5,4-b]indole-2-carboxylic acid ethyl ester (Example 29) is stirred in 20 ml of dimethylformamide with 0.2 g of potassium carbonate for 20 minutes. Thereafter 0.18 g of benzyl chloride is added thereto. The mixture is further stirred under argon overnight, then it is evaporated to a maximum extent under vacuum. The residue is extracted by stirring with water. The water-insoluble proportion yields, after chromatography over silica gel (eluent methylene chloride/ethanol=10:1), the desired 9-benzyloxy-5H-pyrimido[5,4-b]indole-2-carboxylic acid ethyl ester.

EXAMPLE 31

8-Diallylamino-2-(3-ethyl-1.2.4-oxadiazol-5-yl)-5H-pyrimido[5,4-b]indole

A. 150 mg of 8-diallylamino-5H-pyrimido[5,4-b]indole-2-carboxylic acid ethyl ester is hydrolysed by refluxing for 1 hr in 25 ml 90 percent ethanol and 200 mg potassium hydroxide to give 130 mg 8-diallylamino-5H-pyrimido[5,4-b]indole-2-carboxylic acid.

B. 400 mg of propionamide oxime is added to the product of reaction step A. pretreated with 1.5 mMol (6 ml) thionylimidazole in dry tetrahydrofurane. The reaction mixture is left overnight and then concentrated, 20 ml of toluene is added to the residue and the reaction mixture is refluxed for about 2 hours. The hot reaction mixture is then filtered and the filtrate concentrated to give 62 mg of the title compound wi a melting point of 175°-184° C.

Analogously are prepared: 2-(3-ethyl-1,2,4-oxadiazol-5-yl)-5H-pyrimido[5,4-b]indole, m.p. 250°-257° C. was produced from 8-ethoxycarbonyl-5H-pyrimido[5,4-b]indole-2-carboxylic acid ethyl ester, however, by use of double amounts of reagents.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A substituted 5H-pyrimido[5,4-b]indole of the formula

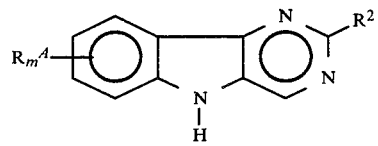

wherein
R$_2$ is halogen, C$_{1-5}$-alkyl, cycloalkyl, of 3-7 carbon atoms, aralkyl of 7-11 carbon atoms, aryl of 5-10 carbon atoms, OR$^I$, SO$_n$R$^I$,

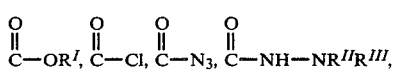

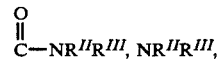

or the oxadiazolyl group

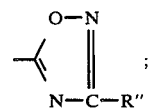

R" is lower alkyl with up to 3 carbon atoms,
R$^{II}$ and R$^{III}$ each independently is hydrogen, C$_{1-5}$-alkyl, C$_{3-5}$-alkenyl, C$_{3-7}$-cycloalkyl, C$_{7-11}$-aralkyl, or C$_{6-10}$-aryl, or together with the connecting N-atom form a 5- or 6-membered heterocyclic ring with 0 or 1 additional hetero atom which is N, O or S;

each R$^A$ independently is halogen, nitro, OR$^I$, SO$_n$R$^I$,

or the oxadiazolyl group

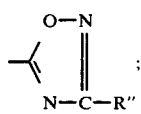

R is C$_{1-5}$-alkyl;
n is 0, 1 or 2;
R$^I$ is hydrogen, C$_{1-5}$-alkyl, C$_{3-7}$-cycloalkyl, C$_{7-11}$-aralkyl, or C$_{6-10}$-aryl;
m is 0, 1, 2, 3 or 4.

2. A substituted 5H-pyrimido[5,4-b]indole of claim 1 wherein m=1 and R$^A$ is in the 8-position.

3. A substituted 5H-pyrimido[5,4-b]indole of claim 1 wherein m=1 and R$^A$ is in the 9-position.

4. A substituted 5H-pyrimido[5,4-b]indole of claim 1 wherein m=2 and the R$^A$'s are in the 8- and 9-positions.

5. A substituted 5H-pyrimido[5,4-b]-indole of claim 1 wherein R$^2$ and/or R$^A$ is the oxadiazolyl group.

6. A compound of claim 1 wherein alkenyl is allyl; cycloalkyl is cyclopentyl or cyclohexyl; aryl is phenyl; aralkyl is benzyl or styryl; and heterocyclic NR$^{II}$R$^{III}$ groups are pyrrolo, pyrrolino, thiazolino, oxazolino, pyrrolidino, piperidino, piperazino, N-methylpiperazino, or morpholino.

7. A compound of claim 1 wherein R$^A$ is nitro, amino, bromo, iodo, diallylamino, diethylphosphoryl, hydroxycarbonyl, chlorocarbonyl, ethoxycarbonyl, methylthio, N,N-dimethylsulfonamido, N,N-dimethylcarbamoyl or N,N-dialylcarbamoyl; R$^2$ is COOH, COOC$_2$H$_5$, or 3-ethyl-1,2,4-oxadiazolyl-5-yl.

8. A compound of claim 1 wherein R$_2$ is halogen, cycloalkyl of 3-7 carbon atoms, aralkyl of 7-11 carbon atoms, aryl of 5-10 carbon atoms,
OR$^I$, SO$_n$R$^I$,

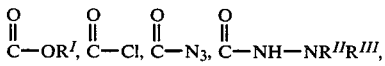

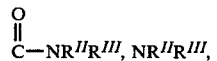

or the oxadiazolyl group

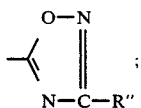

R" is lower alkyl with up to 3 carbon atoms, R$^{II}$ and R$^{III}$ each independently is hydrogen, C$_{1-5}$-alkyl, C$_{3-5}$-alkenyl, C$_{3-7}$-cycloalkyl, C$_{7-11}$-aralkyl, or C$_{6-10}$-aryl, or together with the connecting N-atom form a 5- or 6-membered heterocyclic ring with 0 or 1 additional hetero atom which is N, O or S;

each R$^A$ independently is halogen, nitro, OR$^I$, SO$_n$R$^I$,

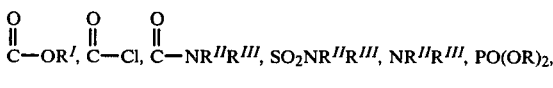

or the oxadiazolyl group

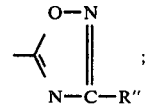

R is C$_{1-5}$-alkyl;
n is 0, 1 or 2;
R$^I$ is hydrogen, C$_{1-5}$-alkyl, C$_{3-7}$-cycloalkyl, C$_{7-11}$-aralkyl, or C$_{6-10}$-aryl;
m is 0, 1, 2, 3 or 4.

9. 2-Methyl-5H-pyrimido[5,4-b]indole, a compound of claim 1.

10. 5H-Pyrimido[5,4-b]indole-2-carboxylic acid, 5H-pyrimido[5,4-b]indole-2-carboxylic acid ethyl ester, 5H-pyrimido[5,4-b]indole-2-carboxylic acid n-propyl ester, 5-pyrimido[5,4-b]indole-2-carboxylic acid hydrazide, or 5H-pyrimido[5,4-b]indole-2-carboxylic acid azide, each a compound of claim 1.

11. 5H-Pyrimido[5,4-b]indole-2-amine, 2-bromo-5H-pyrimido[5,4-b]indole, or 2-chloro-5H-pyrimido[5,4-b]indole, each a compound of claim 1.

12. 6,8-Dinitro-5H-pyrimido[5,4-b]indole-2-carboxylic acid,
6,8-dinitro-5H-pyrimido[5,4-b]indole-2-carboxylic acid ethyl ester,
6- or 8-nitro-5H-pyrimido[5,4-b]indole-2-carboxylic acid ethyl ester,
8-amino-5H-pyrimido[5,4-b]-indole-2-carboxylic acid ethyl ester,
8-diallylamino-5H-pyrimido[5,4-b]indole-2-carboxylic acid ethyl ester, or 8-amino-9-bromo-5H-pyrimido[5,4-b]indole-2-carboxylic acid ethyl ester, each a compound of claim 1.

13. 9-Bromo-5H-pyrimido[5,4-b]indole-2-carboxylic acid ethyl ester,
7- or 9-methoxy-5H-pyrimido[5,4-b]indole-2-carboxylic acid ethyl ester,
9-hydroxy-5H-pyrimido[5,4-b]indole-2-carboxylic acid ethyl ester, or
9-benzyloxy-5H-pyrimido[5,4-b]indole-2-carboxylic acid ethyl ester, each a compound of claim 1.

14. 8-Iodo-5H-pyrimido[5,4-b]indole-2-carboxylic acid ethyl ester,
8-bromo-5H-pyrimido[5,4-b]indole-2-carboxylic acid ethyl ester,
8-N,N-dimethylsulfonamido-5H-pyrimido[5,4-b]indole-2-carboxylic acid ethyl ester,
8-diethylphosphoryl-5H-pyrimido[5,4-b]indole-2-carboxylic acid ethyl ester,
8-benzyloxycarbonyl-5H-pyrimido[5,4-b]indole-2-carboxylic acid ethyl ester,
8-hydroxycarbonyl-5H-pyrimido[5,4-b]indole-2-carboxylic acid ethyl ester,
8-chlorocarbonyl-5H-pyrimido[5,4-b]indole-2-carboxylic acid ethyl ester, 8-N,N-dimethylcarbamoyl-5H-pyrimido[5,4-b]indole-2-carboxylic acid ethyl ester,
8-N,N-diallylcarbamoyl-5H-pyrimido[5,4-b]indole-2-carboxylic acid ethyl ester,
8-ethoxycarbonyl-5H-pyrimido[5,4-b]indole-2-carboxylic acid ethyl ester, or
8-methylthio-5H-pyrimido[5,4-b]indole-2-carboxylic acid ethyl ester, a compound of claim 1.

15. 8-Diallylamino-2-(3-ethyl-1,2,4-oxadiazol-5-yl)-5H-pyrimido[5,4-b]-indole,
2-(3-ethyl-1,2,4-oxadiazol-5-yl)-5H-pyrimido[5,4-b]indole,
2,8-Di-(3-ethyl-1,2,4-oxadiazol-5-yl)-5H-pyrimido[5,4-b]-indole, each a compound of claim 1.

16. A pharmaceutical composition comprising a psychotropically effective amount of a compound of claim 1 and a pharmaceutically acceptable carrier.

17. A composition of claim 14 wherein the amount of active ingredient is 0.05 to 10 mg.

18. A method of achieving a psychotropic effect in a patient in need of such treatment comprising administering to the patient an effective amount of a compound of claim 1.

19. A method of claim 18 wherein the effect is as a tranquilizer.

20. A method of claim 18 wherein the effect is as an antiepileptic.

* * * * *